(12) United States Patent
Shen et al.

(10) Patent No.: US 11,596,493 B2
(45) Date of Patent: Mar. 7, 2023

(54) STRAIN GAUGE, PRESSURE SENSOR, AND INTERVENTIONAL MEDICAL CATHETER

(71) Applicant: SHANGHAI MICROPORT EP MEDTECH CO., LTD., Shanghai (CN)

(72) Inventors: Lei Shen, Shanghai (CN); Tao Miao, Shanghai (CN); Bo Liang, Shanghai (CN); Mei Wang, Shanghai (CN); Hui Wang, Shanghai (CN); Yiyong Sun, Shanghai (CN)

(73) Assignee: SHANGHAI MICROPORT EP MEDTECH CO., LTD., Shanghai (CN)

( * ) Notice: Subject to any disclaimer, the term of this patent is extended or adjusted under 35 U.S.C. 154(b) by 593 days.

(21) Appl. No.: 16/622,743

(22) PCT Filed: Jun. 8, 2018

(86) PCT No.: PCT/CN2018/090483
§ 371 (c)(1),
(2) Date: Dec. 13, 2019

(87) PCT Pub. No.: WO2018/228290
PCT Pub. Date: Dec. 20, 2018

(65) Prior Publication Data
US 2020/0100859 A1    Apr. 2, 2020

(30) Foreign Application Priority Data

Jun. 15, 2017   (CN) .......................... 201710452426.4

(51) Int. Cl.
*A61B 90/00* (2016.01)
*A61B 18/14* (2006.01)
(Continued)

(52) U.S. Cl.
CPC .......... *A61B 90/06* (2016.02); *A61B 18/1492* (2013.01); *G01L 1/2287* (2013.01);
(Continued)

(58) Field of Classification Search
CPC ................ A61B 90/06; A61B 18/1492; A61B 2562/046; A61B 2562/164;
(Continued)

(56) References Cited

U.S. PATENT DOCUMENTS 4,683,755 A    8/1987 Samek
5,369,875 A * 12/1994 Utsunomiya ......... G01L 1/2287
                                                              29/412

(Continued)

FOREIGN PATENT DOCUMENTS

CN        1776385 A      5/2006
CN      101190146 A      6/2008
(Continued)

OTHER PUBLICATIONS

English-language machine translation of CN 1776385, pp. 1-7, 2006 (Year: 2006).*

(Continued)

*Primary Examiner* — Matthew Kremer
*Assistant Examiner* — Om Patel
(74) *Attorney, Agent, or Firm* — Muncy, Geissler, Olds & Lowe, P.C.

(57) ABSTRACT

A strain gauge (10, 40, 50), a pressure sensor (20, 60), and an interventional medical catheter. The strain gauge (10, 40, 50) comprises a substrate (11) and at least two sensitive gages (1, 2) provided on the substrate (11), the at least two sensitive gages (1, 2) being arranged along two mutually perpendicular directions and sharing one ground port (3). The pressure sensor (20, 60) comprises an elastomer (21, 61) and the strain gauge (10, 40, 50) provided on the elastomer (Continued)

(21, 61). The interventional medical catheter comprises a catheter distal end and the pressure sensor (20, 60) provided at the catheter distal end. The present application not only saves the trace space for mounting and using the strain gauge (10, 40, 50) on the interventional medical catheter, facilitating the successful mounting and use of the strain gauge (10, 40, 50) on the interventional medical catheter, improving the adaptability of the strain gauge (10, 40, 50), but also reduces the size of the strain gauge (10, 40, 50), thereby shortening the length of the elastomer (21, 61) of the pressure sensor (20, 60) and reducing the size of the interventional medical catheter.

17 Claims, 10 Drawing Sheets

(51) Int. Cl.
  *G01L 1/22* (2006.01)
  *A61M 25/00* (2006.01)
(52) U.S. Cl.
  CPC . *A61B 2090/065* (2016.02); *A61B 2562/0261* (2013.01); *A61B 2562/046* (2013.01); *A61B 2562/164* (2013.01); *A61M 2025/0002* (2013.01)
(58) Field of Classification Search
  CPC ............................. A61B 2090/064–065; A61B 2562/0261–0266; A61B 2562/04–066; A61B 18/12; A61M 2025/0002; A61M 25/00; G01L 1/2287–2293; G01L 5/1627; G01L 9/006–0061; G01L 9/04; G01L 23/18; G01L 1/22; G01B 7/20; G01B 7/16
  See application file for complete search history.

(56) References Cited

U.S. PATENT DOCUMENTS

| | | | |
|---|---|---|---|
| 2009/0249885 | A1 | 10/2009 | Shkel et al. |
| 2010/0063478 | A1* | 3/2010 | Selkee ................ A61B 5/283 604/524 |
| 2019/0307504 | A1 | 10/2019 | Shen et al. |

FOREIGN PATENT DOCUMENTS

| | | |
|---|---|---|
| CN | 201569670 U | 9/2010 |
| CN | 201594006 U | 9/2010 |
| CN | 201837447 U | 5/2011 |
| CN | 103615967 A | 3/2014 |
| CN | 203657736 U | 6/2014 |
| CN | 105241371 A | 1/2016 |
| CN | 106264719 A | 1/2017 |
| CN | 106606373 A | 5/2017 |

OTHER PUBLICATIONS

English-language machine translation of CN 10524137, pp. 1-5, 2016 (Year: 2016).*

* cited by examiner

STRAIN GAUGE, PRESSURE SENSOR, AND INTERVENTIONAL MEDICAL CATHETER

TECHNICAL FIELD

The present application relates to the technical field of medical equipment, and in particular, to a strain gauge, a force sensor and an interventional medical catheter.

BACKGROUND

For cardiac radiofrequency ablation catheters, strain gauges are generally provided thereon to measure the contact force between distal end of the catheter and the tissue or vessel wall, so as to accurately monitor the implementation process of the ablation treatment, thereby ensuring the successful rate of the operation. Due to the low price, fast response, large measuring range and stable performance, the strain gauge has been widely used in the interventional medical field.

Generally, the strain gauge is made by attaching a metal sensitive grid to a substrate of plastic film. The metal sensitive grid is a set of parallel wires formed by arranging a narrow conductor in a zigzag mode. When stretched, the sensitive grid becomes narrower or longer, and the resistance becomes larger. When compressed, the sensitive grid becomes thicker or shorter, and the resistance becomes smaller. Then, the strain gauge is disposed at the periphery of the elastic body. In this case, when the elastic body is deformed due to the electrode at the top of the elastic body that is subjected to a stress, the sensitive grid of the strain gauge on the elastic body is triggered to become longer or shorter, which in turn causes a corresponding change in resistance.

The resistance strain gauges commonly used on the market are strain gauges based on copper-nickel alloys that generally only have longitudinally arranged sensitive grids and a large circumferential surface area of the grid filament. Although the sensitivity coefficient can reach 2.0, the strain gauges based on copper-nickel alloys are significantly affected by the external temperature. Therefore, the strain gauge can only be used under conditions of dryness, no scouring and tight temperature control. However, for a cardiac radiofrequency ablation catheter, a temperature change of 25-75° C. is generated during the in vivo ablation, resulting in a temperature error of the measurement causes by the corresponding temperature change in the measured circumstance. Two main factors lead to the temperature error of the strain gauge. One is the temperature coefficient of the self-resistance of the sensitive grid and the other is the thermal expansion coefficients of the material of the strain gauge's substrate and the material of the testing material.

In addition, due to the large size of the existing strain gauge, the application of the strain gauge to the ablation catheter has been limited in a certain degree for that the strain gauges cannot be fitted with the ablation catheter in the axial direction.

Therefore, since the existing strain gauges have certain limitations, it is necessary to develop a strain gauge that has a small size, an easy installation on the interventional medical catheter, and a good performance in precision and sensitivity, as well as an insusceptible property by temperature.

SUMMARY

It is an object of the present application to provide a strain gauge, a force sensor and an interventional medical catheter for solving the problem that the strain gauge on the existing interventional medical catheter has a large size and certain limitations in application.

To achieve the foregoing object, the present application provides a strain gauge, comprising a substrate and at least two sensitive grids disposed on the substrate, wherein the at least two sensitive grids are arranged in two directions that are perpendicular to each other and share one grounding interface.

Optionally, the sensitive grid comprises at least one longitudinal sensitive grid and at least one lateral sensitive grid. The substrate has a first direction and a second direction. The first direction is one of a length direction of the substrate and a width direction of the substrate, and the second direction is the other one of the length direction of the substrate and the width direction of the substrate. The at least one longitudinal sensitive grid is disposed along the first direction, and the at least one lateral sensitive grid is disposed along the second direction.

Optionally, one longitudinal sensitive grid and one lateral sensitive grid are provided, and the grid width of the one longitudinal sensitive grid is aligned with the grid length of the one lateral sensitive grid, or the grid length of the one longitudinal sensitive grid is aligned with the grid width of the one lateral sensitive grid.

Optionally, a plurality of longitudinal sensitive grids are provided, and at least one lateral sensitive grid is provided. The plurality of longitudinal sensitive grids are parallel to and aligned with each other and arranged along the first direction, and one lateral sensitive grid is disposed between two adjacent longitudinal sensitive grids. All of the longitudinal sensitive grids and the lateral sensitive grid share one grounding interface.

The grid width of the longitudinal sensitive grid is aligned with the grid length of the lateral sensitive grid, or the grid length of the longitudinal sensitive grid is aligned with the grid width of the lateral sensitive grid.

Optionally, all of the sensitive grids share a grounding lead, the grounding lead is connected to the grounding interface, and all of the sensitive grids are integrally formed.

Optionally, the one shared grounding lead is located on the medial axis of the substrate, and the medial axis is parallel to one of the length direction and the width direction of the substrate.

Optionally, each sensitive grid further has one non-grounding interface. The non-grounding interface of each sensitive grid is connected to one non-grounding lead. All of the grounding leads and all of the non-grounding leads are arranged in parallel and extending towards a same direction.

Optionally, the longitudinal sensitive grids and the lateral sensitive grids are equal in grid width and grid length, and all of the longitudinal sensitive grids and the lateral sensitive grids have a same grid structure.

Optionally, the substrate is a semi-rigid substrate.

Optionally, the material of the substrate is selected from one or more of the group consisting of polyimide and polyetheretherketone.

Optionally, each of the length and the width of the substrate are not greater than 2.0 mm.

Further, the present application also provides a force sensor, comprising an elastic body and at least one strain gauge as defined above, wherein the at least one strain gauge is disposed on the elastic body.

Optionally, a plurality of strain gauges are provided. The plurality of strain gauges are arranged on different circumferences of the elastic body along the axial direction of the elastic body and are circumferentially arranged in a staggered manner. The longitudinal sensitive grids of the respective strain gauges are arranged along the axial direction of the elastic body. The lateral sensitive grid of the respective strain gauges are arranged along the circumferential direction of the elastic body.

Optionally, the orthographic projections of the plurality of strain gauges in a same plane in the axial direction are uniformly distributed in the circumferential direction.

Optionally, a plurality of strain gauges are provided, and the plurality of strain gauges comprise at least a first strain gauge and a second strain gauge.

The first strain gauge includes one substrate, one longitudinal sensitive grid, and one lateral sensitive grid. The one longitudinal sensitive grid is arranged along the axial direction of the elastic body. The one lateral sensitive grid is arranged along the circumferential direction of the elastic body.

The second strain gauge includes another one substrate, a plurality of longitudinal sensitive grids, and at least one lateral sensitive grid. The plurality of longitudinal sensitive grids are parallel to and aligned with each other and arranged along the axial direction of the elastic body, and one lateral sensitive grid is disposed between two adjacent longitudinal sensitive grids. The at least one lateral sensitive grid is arranged along the circumferential direction of the elastic body, and all of the longitudinal sensitive grids and the lateral sensitive grids of the second strain gauge share one grounding interface.

Optionally, a plurality of hollow grooves are formed on the elastic body. Each hollow groove extends along the circumferential direction of the elastic body. The plurality of hollow grooves are located on different circumferences along the axial direction of the elastic body and are circumferentially arranged in a staggered manner, and one strain gauge is disposed between opposite ends of each hollow groove.

Optionally, each of the opposite ends of each hollow groove is provided with one axial groove that extends along the axial direction of the elastic body.

Optionally, the sensitive grid of the strain gauge is aligned with the axial groove along the axial direction of the elastic body.

Further, the present application also provides an interventional medical catheter, comprising a catheter distal end, wherein the catheter distal end is provided with the force sensor as defined above.

Optionally, the interventional medical catheter further comprises an electrode connected to the force sensor. The force sensor includes a first strain gauge and a second strain gauge. The first strain gauge includes one substrate, one longitudinal sensitive grid, and one lateral sensitive grid. The one longitudinal sensitive grid is arranged along the axial direction of the catheter. The one lateral sensitive grid is arranged along the circumferential direction of the catheter. The second strain gauge includes another one substrate, a plurality of longitudinal sensitive grids, and at least one lateral sensitive grid. The plurality of longitudinal sensitive grids are parallel to and aligned with each other and arranged along the axial direction of the catheter, and one lateral sensitive grid is disposed between two adjacent longitudinal sensitive grids. The at least one lateral sensitive grid is arranged along the circumferential direction of the catheter, and all of the longitudinal sensitive grids and the lateral sensitive grids of the second strain gauge share one grounding interface. The first strain gauge is closer to the electrode than the second strain gauge.

In summary, in the strain gauge, the force sensor and the interventional medical catheter provided in the present application, all sensitive grids of the strain gauge share one grounding interface allowing to reduce the number of grounding interfaces on the strain gauge. Therefore, the present application can not only save the wiring space for mounting the strain gauge on the interventional medical catheter, to facilitate the successful mounting of the strain gauge on the interventional medical catheter and to improve the adaptability of the strain gauge, but also reduce the size of the strain gauge, which in turn shortens the length of the elastic body of the force sensor as well as reduces the size of the interventional medical catheter.

Moreover, according to a preferred embodiment of the present application, a plurality of longitudinal sensitive grids are able to be arranged on one substrate of one strain gauge, the plurality of longitudinal sensitive grids being arranged along a same direction, one lateral sensitive grid being further arranged between two adjacent longitudinal sensitive grids, and all the sensitive grids sharing one grounding interface. Such an arrangement allows to reduce the number of strain gauges used on the force sensor, (i.e., the number of strain gauges is able to be reduced from at least three to at least two), thereby enabling to reduce the length of the force sensor, and in turn shorten the length of the distal end of the interventional medical catheter and cut down the cost of use.

In addition, in the strain gauge according to a preferred embodiment of the present application, all the sensitive grids are configured to share one grounding interface, and the whole size of the strain gauge integrated with the plurality of longitudinal sensitive grids is reduced, so that the length of the hollow groove provided on the elastic body of the force sensor allows to be processed longer along the circumferential direction of the elastic body, and thus the strain gauge located between opposite ends of the hollow groove is able to sense a stronger strain signal. In this case, a better measurement is achieved.

1, 2—sensitive grid; 3—grounding interface; 4—non-grounding interface;
10, 40, 50—strain gauge; 11—substrate; 12—longitudinal sensitive grid; 121—grid structure; 122—non-grounding interface; 123—grounding interface; 124—non-grounding lead; 125—grounding lead; 13—lateral sensitive grid;
20, 60—force sensor; 21, 61—elastic body; 211, 611—hollow groove; 212, 612—axial groove;
30—ablation electrode.

DETAILED DESCRIPTION OF THE INVENTION

Figure 1:
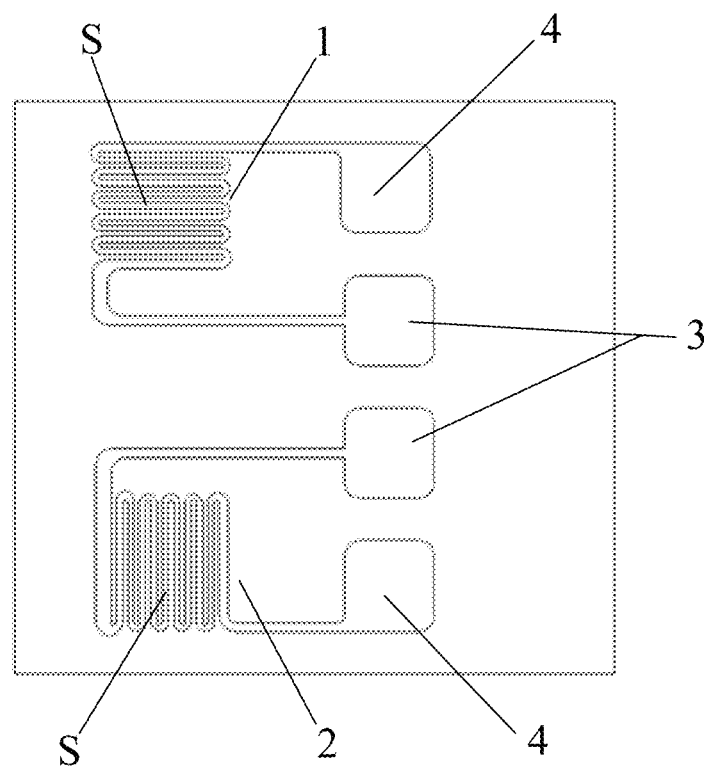
FIG. 1 is a schematic structural diagram of a conventional strain gauge in which a longitudinal sensitive grid and a lateral sensitive grid are independent of each other.

FIG. 1 provides a schematic structural diagram of an existing strain gauge. As shown in FIG. 1, the strain gauge includes two sensitive grids 1, 2. For any one of the sensitive grids, one grid structure S, one grounding interface 3, one non-grounding interface 4, one grounding lead connected to the grounding interface 3 (the grounding lead is a grid filament connected to one end of the grid structure S of the sensitive grid), and one non-grounding lead connected to the non-grounding interface 4 (the non-grounding lead is also a grid filament connected to the other end of the grid structure S) are provided. The grounding interface 3 of any one of the sensitive grids can be further connected to a power grounding end through a wire, and the non-grounding interface 4 of any one of the sensitive grids can be further connected to a power output end through a wire.

In actual use, one sensitive grid 1 is used to sense the strain of a measured object in a first direction (such as the axial direction), and the other sensitive grid 2 is used to sense the strain of the measured object in a second direction that is perpendicular to the first direction (such as the circumferential direction). For example, the sensitive grid 1 is arranged along the axial direction of the measured object such that it can be elongated or contracted in a direction parallel to the axial direction of the measured object. The sensitive grid 2 is arranged in the circumferential direction of the measured object such that it can be elongated or contracted in a direction parallel to the circumferential direction of the measured object.

However, the inventor finds through research that there are some problems with the foregoing strain gauges. Specifically, the two sensitive grids 1 and 2 have four interfaces in total. In actual use, the four interfaces are connected to an external power supply through a wire, respectively. It is obvious that, in this case, lots of wires are required for connection, resulting in an increased wiring space of the strain gauge on the interventional medical catheter, which in turn increases the size of the interventional medical catheter. In addition, since the grounding interfaces of the two sensitive grids 1 and 2 are independent of each other (i.e., connected to the grid structure S through one grounding lead, respectively), when two sensitive grids 1 and 2 are arranged, the spacing formed therebetween is relatively large. Therefore, the size of the strain gauge is increased, and accordingly, the size of the corresponding interventional medical catheter is also increased, which in turn limits the successful use of the strain gauge on the interventional medical catheter.

Therefore, based on the technical problems existed in the foregoing strain gauge, the present application provides a strain gauge, which not only allows to reduce the number of grounding interfaces used so as to decrease the overall size of the strain gauge, but also enables to reduce the number of strain gauges used on the force sensor so as to decrease the length of the force sensor can be shortened, as well as the size of the interventional medical catheter. In this case, the application limitations of the strain gauge on the interventional medical catheter are overcome, thereby improving the adaptability of the strain gauge and thus promoting the success rate of the interventional treatment.

In order to make the content of the present application more apparent and easier to be understood, the strain gauge, the force sensor and the interventional medical catheter proposed in the present application will be further described in detail with reference to the accompanying FIG. 2-FIG. 16. Certainly, the present application is not limited to the specific embodiments, and general substitutions well known to those skilled in the art also fall within the protection scope of the present application.

Then, the present application is described in detail with reference to schematic diagrams. However, the schematic diagrams are only for the purpose of illustrating the examples of the present application and are not intended to limit the present application.

As used herein, a "proximal end" and a "distal end" are opposing orientations, positions and directions of elements or actions relative to each other from the perspective of a surgeon using the product. Although the "proximal end" and the "distal end" are not restrictive, the "proximal end" generally refers to the end of the product that is close to the surgeon during normal operation, while the "distal end" generally refers to the end that enters into the patient at first. The "axial direction" and the "circumferential direction" refer to the axial direction and the circumferential direction of the elastic body, respectively.

As used in the specification and the appended claims, the singular forms "a" and "the" include plural objects, unless otherwise explicitly stated. As used in the specification and the appended claims, the term "or" is used in the meaning of "and/or", unless otherwise explicitly stated.

Embodiment 1

Figure 2:
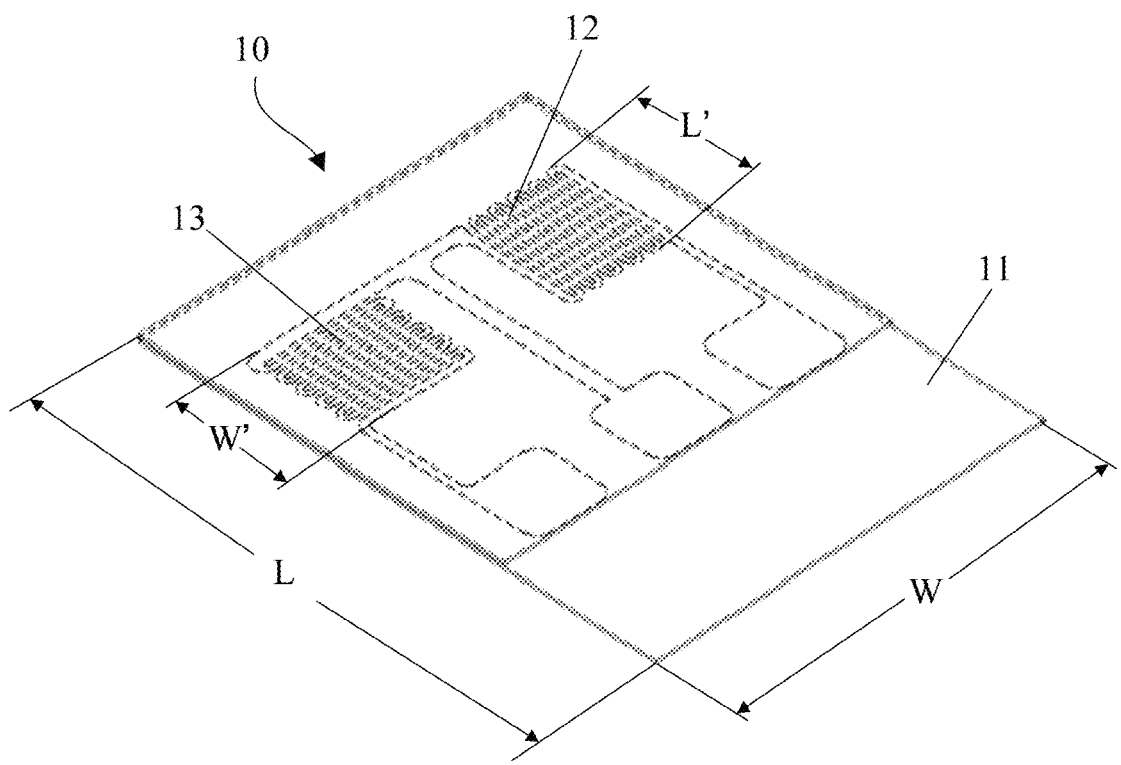
FIG. 2 is an isometric view of a strain gauge according to Embodiment 1 of the present application.
Figure 3:
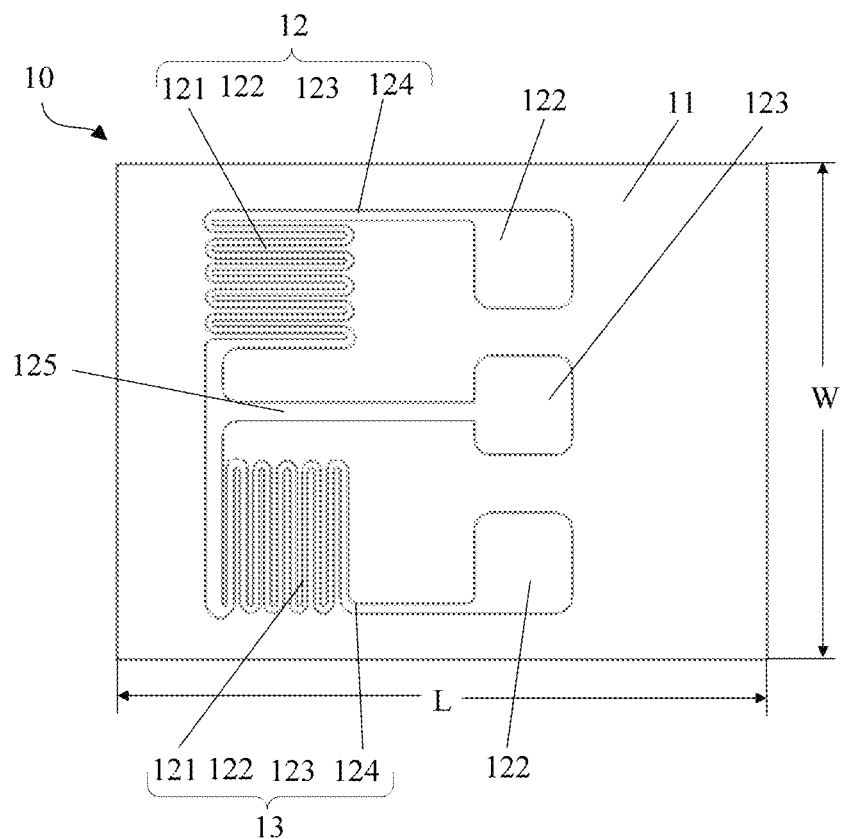
FIG. 3 is a top view of the strain gauge shown in FIG. 2.

FIG. 2 is an isometric view of a strain gauge 10 according to Embodiment 1 of the present application. FIG. 3 is a top view of the strain gauge 10 shown in FIG. 2. As shown in FIG. 2 and FIG. 3, the strain gauge 10 includes a substrate 11, and a longitudinal sensitive grid 12 and a lateral sensitive grid 13 that are disposed on the substrate 11. Here, the longitudinal sensitive grid 12 is generally arranged along the axial direction of the measured object (i.e., the direction of the grid length L' of the longitudinal sensitive grid is parallel to the axial direction of the measured object, and the direction of the grid width W' of the longitudinal sensitive grid is parallel to the circumferential direction of the measured object), and the lateral sensitive grid 13 is arranged along the direction that is perpendicular to the axial direction of the measured object (i.e., the direction of the grid width W' of the lateral sensitive grid is parallel to the axial direction of the measured object, and the direction of the grid length L' of the lateral sensitive grid is parallel to the circumferential direction of the measured object), similarly hereinafter.

In this embodiment, the longitudinal sensitive grid 12 is arranged along one of the length direction and the width direction of the substrate 11, and the lateral sensitive grid 13 is arranged along the other of the length direction and the width direction of the substrate 11. Hereinafter, for ease of description, further description is made by taking the case that the longitudinal sensitive grid 12 is arranged along the length direction of the substrate 11, and the lateral sensitive grid 13 is arranged along the width direction of the substrate 11 as an example.

Herein, the length of the substrate 11 is defined as L, and the width of the substrate 11 is defined as W. The direction of the grid length L' of the longitudinal sensitive grid 12 is parallel to the length direction of the substrate 11, and the direction of the grid width W' of the lateral sensitive grid 12 is parallel to the length direction of the substrate 11. In actual use, the length direction of the substrate 11 may be parallel to the axial direction of the measured object, so that the two sensitive gratings can sense the strain of the measured object in the axial direction and the circumferential direction that is perpendicular to the axial direction (in this case, the measured object is schematically defined to have a shape of a cylinder, a truncated cone, a cuboid or other pillar). It is obvious that under the action of strain, the two sensitive gratings are deformed in opposite ways. That is, when one of the sensitive gratings is elongated to deform along its length direction, the other sensitive grid is shortened to deform along its length direction. Specifically, when the measured object is stretched along the length direction of the substrate 11, the longitudinal sensitive grid 12 becomes longer along the stretching direction, and the lateral sensitive grid 13 becomes shorter along a direction perpendicular to the stretching direction. In other words, the elongation and contraction direction of the longitudinal sensitive grid 12 is parallel to the length direction of the substrate 11, and the elongation and contraction direction of the lateral sensitive grid 13 is parallel to the width direction of the substrate 11.

Each sensitive grid includes one grid structure 121, one non-grounding interface 122, one grounding interface 123, one non-grounding lead 124, and one grounding lead 125. The grid structure 121 is a set of parallel wires formed by arranging a narrow conductor in a zigzag mode, and the set of parallel wires has a grid shape. For any sensitive grid, the non-grounding interface 122 and the grounding interface 123 are respectively disposed at opposite ends of the grid structure 121 and the non-grounding interface 122 is connected to one end of the grid structure 121 through the non-grounding lead 124. The non-grounding lead 124 is formed by extending the foregoing parallel wire. The grounding interface 123 is connected to the other end of the grid structure 121 through the grounding lead 125. The grounding lead 125 can also be formed by extending the parallel wire of the grid structure.

Furthermore, in order to save the number of grounding interfaces of the strain gauge connected to the grounding end of the external power supply, the longitudinal sensitive grid 12 and the lateral sensitive grid 13 are configured to share one grounding interface 123. The shared grounding interface 123 can be connected to the grounding end of the external power supply through a wire, and can be connected to each of the grid structure 121 of the longitudinal sensitive grid 12 and the grid structure 121 of the lateral sensitive grid 13 through a same grounding lead 125. In such an arrangement, the number of interfaces are decreased from four to three, thereby reducing the number of wires of the strain gauge connected to the external power supply. Therefore, not only the wiring space for mounting the strain gauge on the interventional medical catheter is saved, so as to facilitate the successful mounting and use of the strain gauge on the interventional medical catheter, and improve the adaptability of the strain gauge, but also the size of the strain gauge is accordingly reduced due to the decreased number of interfaces, which in turn reduces the sizes of the force sensor and the interventional medical catheter with strain gauges, and helps in reducing the cost of interventional treatment and the probability of infection in patients to improve the success rate of the intervention treatment.

Preferably, all the sensitive grids are integrally formed to further reduce the size of the strain gauge.

In this embodiment, the longitudinal sensitive grid 12 and the lateral sensitive grid 13 are preferably parallel to and aligned with each other. That is, one of the grid width W' and the grid length L' of the longitudinal sensitive grid 12 is aligned with the other of the grid width W' and the grid length L' of the lateral sensitive grid 13. As shown in FIG. 2, the grid length L' of the longitudinal sensitive grid 12 is aligned with the grid width W' of the lateral sensitive grid 13 when the longitudinal sensitive grid 12 is arranged along the length direction of the substrate 11. That is, the projection of the grid length L' of the longitudinal sensitive grid 12 in the length direction of the substrate 11 coincides with the grid width W' of the lateral sensitive grid 13 when the longitudinal sensitive grid 12 is arranged along the length direction of the substrate 11. In other embodiments, the grid width W' of the longitudinal sensitive grid 12 is aligned with the grid length L' of the lateral sensitive grid 13 when the longitudinal sensitive grid 12 is arranged along the width direction of the substrate 11. That is, the projection of the grid width W' of the longitudinal sensitive grid 12 in the length direction of the substrate 11 coincides with the grid length L' of the lateral sensitive grid 13.

More specifically, the longitudinal sensitive grid and the lateral sensitive grid that are parallel to and aligned with each other can eliminate the influence of temperature drift on the strain gauge in the axial direction of the interventional medical catheter when the length direction of the substrate 11 is parallel to the axial direction of the measured object, e.g., the interventional medical catheter. That is, the lateral sensitive grid 13 and the longitudinal sensitive grid 12 that are parallel to and aligned with each other can provide temperature compensation for the strain gauge 10. Here, the "temperature drift" refers to changes in parameters of the strain gauge caused by temperature changes in measured circumstance, which may cause an unstable measurement result due to the instability of an output signal from the strain gauge, and even lead to a non-work state of the strain gauge. For example, for a radiofrequency ablation catheter, the temperature generated by the distal ablation electrode during the in vivo ablation is conducted in the direction from the proximal end to the distal end of the catheter, resulting in different temperatures in the axial direction of the catheter. That is, the catheter has different temperatures at different axial heights. Therefore, in order to eliminate the effects of temperature drift at the same measurement temperature, the two sensitive grids are arranged in parallel to and alignment with each other in the axial direction of the catheter. In addition to the elimination of temperature drift, the longitudinal sensitive grid 12 and the lateral sensitive grid 13 that are arranged in parallel to and alignment with each other (i.e., at a same axial height), enable to achieve a better sense of strain for each sensitive grid, thereby improving the output strength of signal and further reducing the size of the strain gauge 10.

In order to obtain a strain gauge 10 with a small size, three leads 124, 125 are arranged in parallel and extending towards a same direction, preferably extending towards the proximal end of the interventional medical catheter, and the extension direction is parallel to the axial direction of the interventional medical catheter. Referring to FIG. 3, the longitudinal sensitive grid 12 and the lateral sensitive grid 13 are arranged in parallel to each other in the width direction of the substrate 11, and in alignment with each other in the length direction of the substrate 11, thereby ensuring that the two sensitive grids can eliminate the impact of temperature drift during contact force measurement.

More preferably, each of the longitudinal sensitive grid 12 and the lateral sensitive grid 13 is arranged in a square profile. That is, the maximum size of the profile in the length direction of the substrate 11 is consistent with the maximum size of the profile in the width direction of the substrate 11. More specifically, the size and shape of the grid structure 121 of the longitudinal sensitive grid 12 and the grid structure 121 of the lateral sensitive grid 13 are preferably the same. In addition, the grid structure 121 of each sensitive grid is more preferably square, i.e., the grid width W' is equal to the grid length L', so that the length and width of the strain gauge can be reduced at the same time to make the size of the strain gauge smaller. Optionally, the grid structure 121 of each sensitive grid can be made of an etched nickel-chromium alloy foil. More optionally, each sensitive grid has a sensitivity coefficient of 2.2 and a resistance value between 120Ω and 350Ω for obtaining the strain gauge with better sensitivity and precision.

Optionally, the grounding lead 125 connected to the common grounding interface 123 is located on the medial axis of the substrate 11 (i.e., the grounding lead 125 is collinear with the medial axis). The medial axis is parallel to one of the length and width directions of the substrate 11. Taking the grounding lead 125 as a reference line of installation, the mounting position of the strain gauge can be determined according to the reference line. Moreover, in actual installation, the medial axis is parallel to the axial direction of the measured object, so that the two sensitive grids sense the strain of the measured object at the same axial height of the measured object.

In this embodiment, the substrate 11 is preferably made of a semi-rigid plastic material. For example, the material of the substrate 11 is selected from one or more of special molecular materials, i.e., Polyimide (PI) and Polyetheretherketone (PEEK). More preferably, the substrate 11 is processed from the PEEK material so that the substrate 11 has excellent rigidity and flexibility. Optionally, the substrate 11 has a thickness in a range of 5 μm to 10 μm, so as to have a certain flexibility. Optionally, the length and width of the substrate 11 are not greater than 2.0 mm. Preferably, the width is in a range of 1.5 mm to 2.0 mm, and the size of the substrate is small, so as to facilitate the installation of the strain gauge.

Further, the strain gauge 10 also includes a cover film (not shown) covering each sensitive grid. In addition, the cover film can be made of the PEEK material. When both the semi-rigid substrate 11 and the cover film have certain flexibility, the strain gauge 10 can be used on a surface having a high curvature to facilitate the installation and use of the strain gauge.

Figure 4:
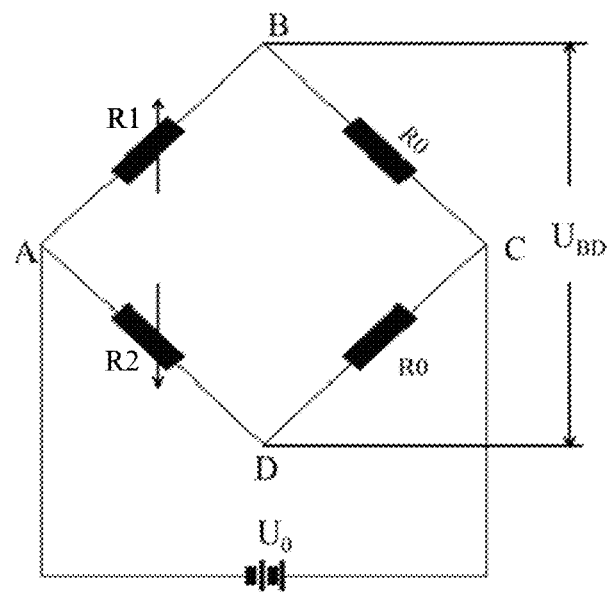
FIG. 4 is a Wheatstone half-bridge circuit composed of the strain gauge shown in FIG. 2.

Next, referring to FIG. 4, showing a Wheatstone half-bridge circuit formed by the strain gauge 10 shown in FIG. 2 and FIG. 3, where R0 is a fixed resistor, U0 is a power voltage, and UBD is an output voltage (i.e., an electric signal output by the half-bridge circuit), R1 represents the longitudinal sensitive grid 12, and R2 represents the lateral sensitive grid 13.

As shown in FIG. 4, the changes of the resistance values of R1 and R2 can be amplified into voltage changes by the Wheatstone half-bridge circuit, and the direction and magnitude of the stress on the measured object can be determined by the change of the voltage.

$$where\ U_{BD}=U_{BA}-U_{AD}$$

$U_{BA}$ is a voltage of R1, and $U_{AD}$ is a voltage of R2.

Further, the magnitude of the strain reflected by $U_{BD}$ is:

When the grid filament of the longitudinal sensitive grid 12 is elongated, the resistance of R1 increases, i.e., corresponding to the positive strain $\varepsilon_{force1}$. Moreover, when the grid filament of the lateral sensitive grid 13 is shortened, the resistance of R2 decreases, i.e., corresponding to the negative strain $\varepsilon_{force2}$.

Therefore, according to Poisson's ratio principle of material:

$$\varepsilon_{force}=\varepsilon_{force1}-\varepsilon_{force2}$$

where V is Poisson's ratio, and is generally 0.33. That is, $\varepsilon_{force}=1.33*\varepsilon_{force1}$.

Compared with the single-bridge circuit, the electrical signal output by the Wheatstone half-bridge circuit has a higher quality, which is 1.33 times of the electrical signal output by the ordinary single-bridge circuit.

Figure 5:
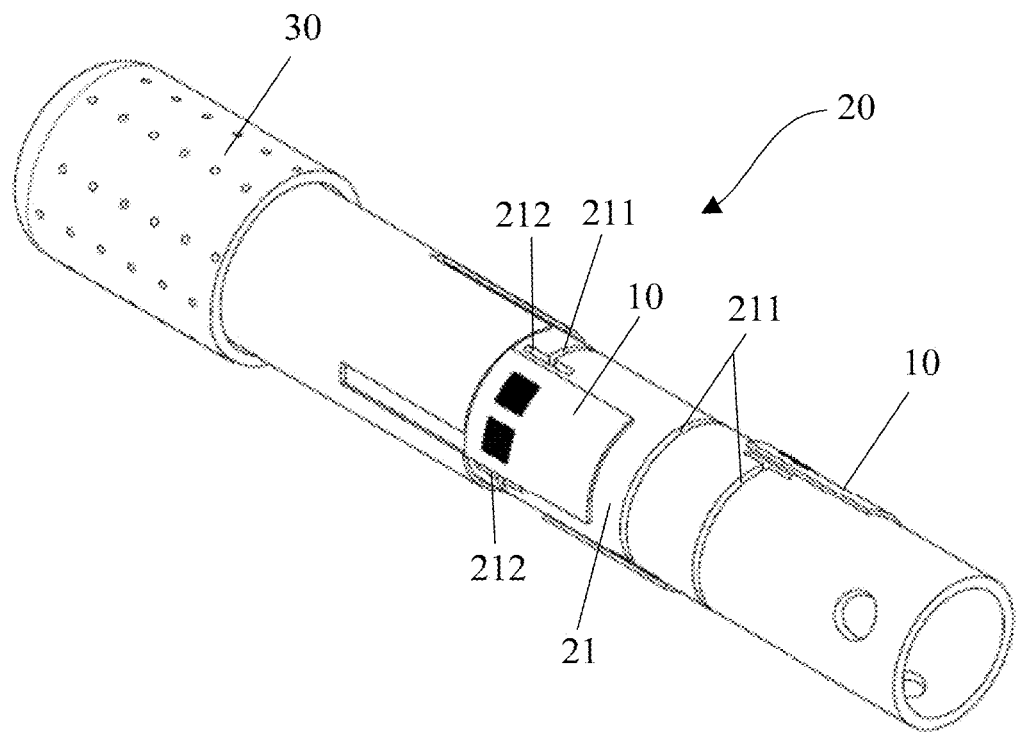
FIG. 5 is a schematic structural diagram of a force sensor according to Embodiment 1 of the present application in connection with an electrode.
Figure 6:
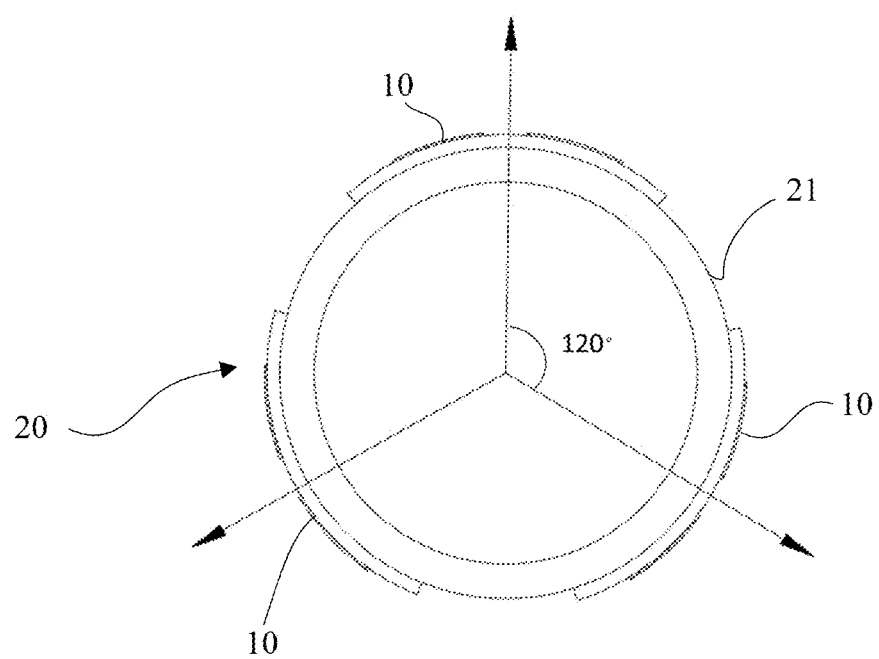
FIG. 6 is a schematic diagram of three strain gauges according to Embodiment 1 of the present application uniformly distributed on an elastic body.
Figure 7:
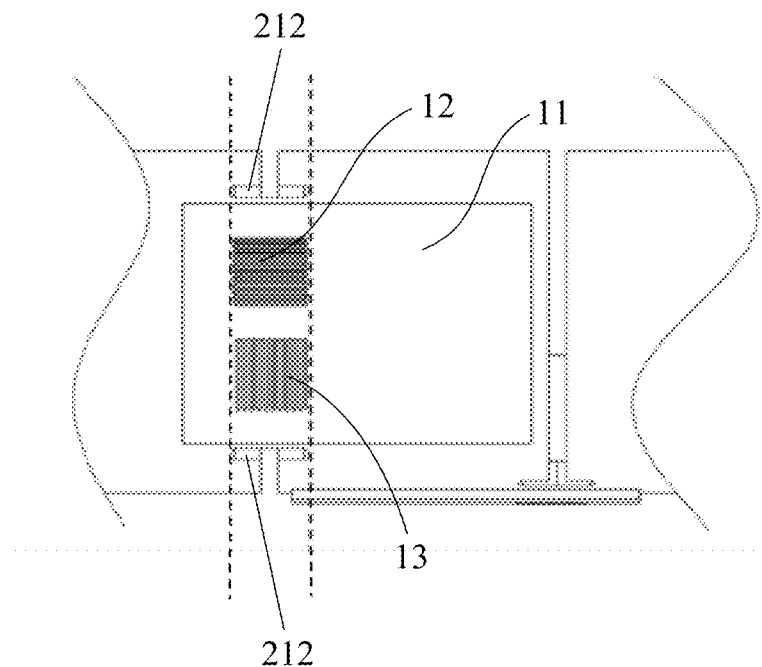
FIG. 7 is a schematic diagram of a strain gauge according to Embodiment 1 of the present application mounted on an elastic body.

Furthermore, this embodiment also provides a force sensor 20, specifically as shown in FIG. 5-FIG. 7. FIG. 5 is a schematic structural diagram of the force sensor 20 according to Embodiment 1 of the present application in connection with an ablation electrode 30. FIG. 6 is a schematic diagram of three strain gauges 10 uniformly distributed on an elastic body 21 of the force sensor 20. FIG. 7 is a schematic diagram showing the position where the strain gauge 10 is pasted on the elastic body 21. The following embodiments are schematically illustrated with the elastic body 21 as a cylindrical hollow elastic body herein.

Specifically, the force sensor 20 includes an elastic body 21 and at least three strain gauges 10. The at least three strain gauges 10 are disposed on the outer surface of the elastic body 21 to sense the axial and circumferential strains at least at three different positions of the elastic body 21. The at least three strain gauges 10 are preferably located on different circumferences and are circumferentially arranged in a staggered manner.

The strain gauges 10 of this embodiment are preferably selected to be three, which can control the cost and avoid increasing the catheter volume under the premise of satisfying the actual requirements of contact force measurement. As shown in FIG. 6, the projections of the three strain gauges 10 in the same plane are preferably uniformly distributed along the circumferential direction of the elastic body 21. That is, the orthographic projections of the three strain gauges 10 in the same plane are uniformly arranged at 120° along the circumferential direction.

The following embodiments further illustrate the technical solution of the present application by taking the structures of three strain gauges 10 as an example. The technical solution of the present application includes, but not limited to three strain gauges 10, and three or more strain gauges 10. The orthographic projections of three or more strain gauges in the same plane are also preferably uniformly distributed along the circumferential direction of the elastic body 21.

Still referring to FIG. 5, the distal end of the elastic body 21 can be connected to the ablation electrode 30. For example, the ablation electrode 30 is fixed on the outer surface of the elastic body 21 through epoxy or acrylic glue, or by welding. The elastic body 21 can be a flexible plastic or rubber tube or a cut metal tube. The preferred material for the plastic or rubber tube is a polymer material such as TPU, PVC, PEBAX, nylon, silicone rubber or natural rubber. The metal tube is preferably made of a metal material having a shape memory function such as nickel-titanium alloy or stainless steel. The metal tube can be cut in such a manner that a hollow portion (i.e., a hollow groove is formed by cutting through the outer wall of the elastic body 21) is formed on the surface of the tube body. The hollow portion can be a hollow groove in the circumferential direction or the axial direction of the elastic body 21, or a spiral hollow groove formed by other cutting methods that can impart elasticity to the metal tube.

In this embodiment, the elastic body 21 preferably has three hollow grooves 211 cut in the circumferential direction, and a strain gauge 10 is preferably disposed between opposite ends of each hollow groove 211. In the embodiments of the present application, three hollow grooves 211 are located on different circumferences in the axial direction and are circumferentially arranged in a staggered manner. More preferably, the projections of the three hollow grooves 211 in the same plane are preferably uniformly distributed in the circumferential direction of the elastic body 21, i.e., the orthographic projections of the three hollow grooves 211 in the same plane are uniformly arranged at 120° in the circumferential direction.

In a preferred solution, each of opposite ends of each hollow groove 211 is provided with one axial groove 212. The axial groove 212 extends along the axial direction of the elastic body 21, and the length of axial groove 212 along the axial direction of the elastic body 21 is not less than the grid width W' or the grid length L' of the sensitive grid. Preferably, the length of the axial groove 212 along the axial direction of the elastic body 21 is equal to the grid width W' or the grid length L'. The consistence of the two sizes helps in indicating the paste position of the strain gauge 10. Moreover, the grid structure 121 (i.e., the grid region) of the strain gauge 10 has the maximum strain in the region corresponding to the axial groove 212, resulting in a stronger output signal, and a better measurement effect. In actual installation, as shown in FIG. 7, the grid length L' of the longitudinal sensitive grid 12 is preferably aligned with the axial groove 212 along the axial direction of the elastic body 21, and the grid width W' of the lateral sensitive grid 13 is aligned with the axial groove 212 along the axial direction of the elastic body 21.

In addition, each strain gauge 10 is preferably disposed on the same circumference as the hollow groove 211. Specifically, for one strain gauge 10, the center line of each sensitive grid along the circumferential direction of the elastic body 21 and the center line of the corresponding hollow groove 211 along the circumferential direction are on the same circumference, so that the strain can be better sensed. In addition, the experimental results show that when the medial axis of the strain gauge 10 along the axial direction of the elastic body 21 is parallel to the axis of the elastic body 21, and the sensitive grid thereof is aligned with the axial groove 212, the strain gauge 10 senses the largest strain, and the output signal is the strongest. Therefore, the measurement is the most accurate.

Generally, the longer the length of the hollow groove cut along the circumferential direction is, the stronger the strain electrical signal sensed by the strain gauge of the present application is. Therefore, when the size of the strain gauge provided in the present application (the size of the strain gauge can be the width W or the length L herein) is reduced, for example, by 0.5 mm in width, it is advantageous to form a longer hollow groove in the circumferential direction, so that the strain electrical signal sensed by the strain gauge is correspondingly stronger. In addition, compared with the prior art, the strain gauge provided in the present application can also reduce the number of interfaces provided thereon, and correspondingly reduce the number of wires connected to the interfaces. For example, for strain gauges having longitudinal and lateral sensitive grids, at least one 38 AWG wire can be reduced. Therefore, for the entire interventional medical catheter, the wiring space inside the catheter is greatly saved, which not only facilitates wiring, but also reduce the size of the catheter.

Figure 8:
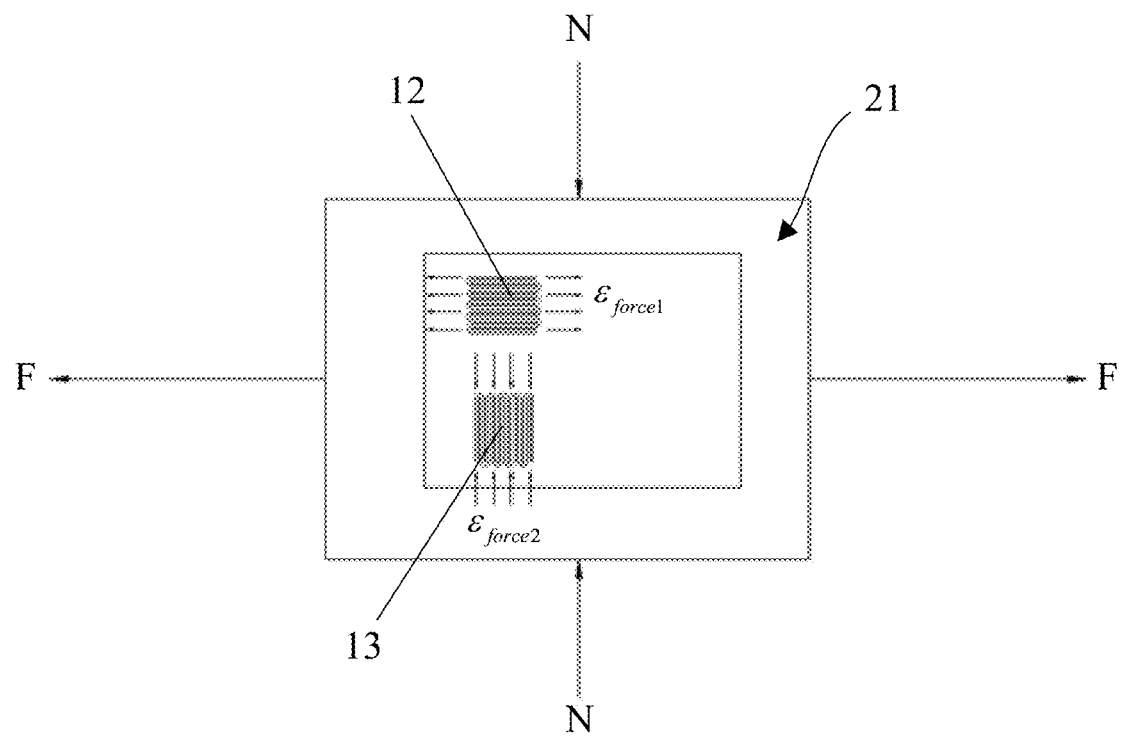
FIG. 8 is a strain schematic diagram of a grid filament when the elastic body according to Embodiment 1 of the present application is subjected to a tensile stress.

Next, the principle of strain measurement of this embodiment will be described in more detail with reference to FIG. 8 and FIG. 9. First, referring to FIG. 8, when the elastic body 21 of the force sensor 20 is stretched in the axial direction by the stress F, the grid filament of the longitudinal sensitive grid 12 is elongated, and the resistance of R1 is increased to generate a positive strain $\varepsilon_{force1}$. Moreover, when the lateral sensitive grid 13 is compressed in the circumferential direction by the stress N, the grid filament is shortened, and the resistance of R2 is decreased to generate a negative strain $\varepsilon_{force2}$. Then, the strain $\varepsilon_{force}$ can be finally obtained according to $\varepsilon_{force1}$ and $\varepsilon_{force2}$.

Figure 9:
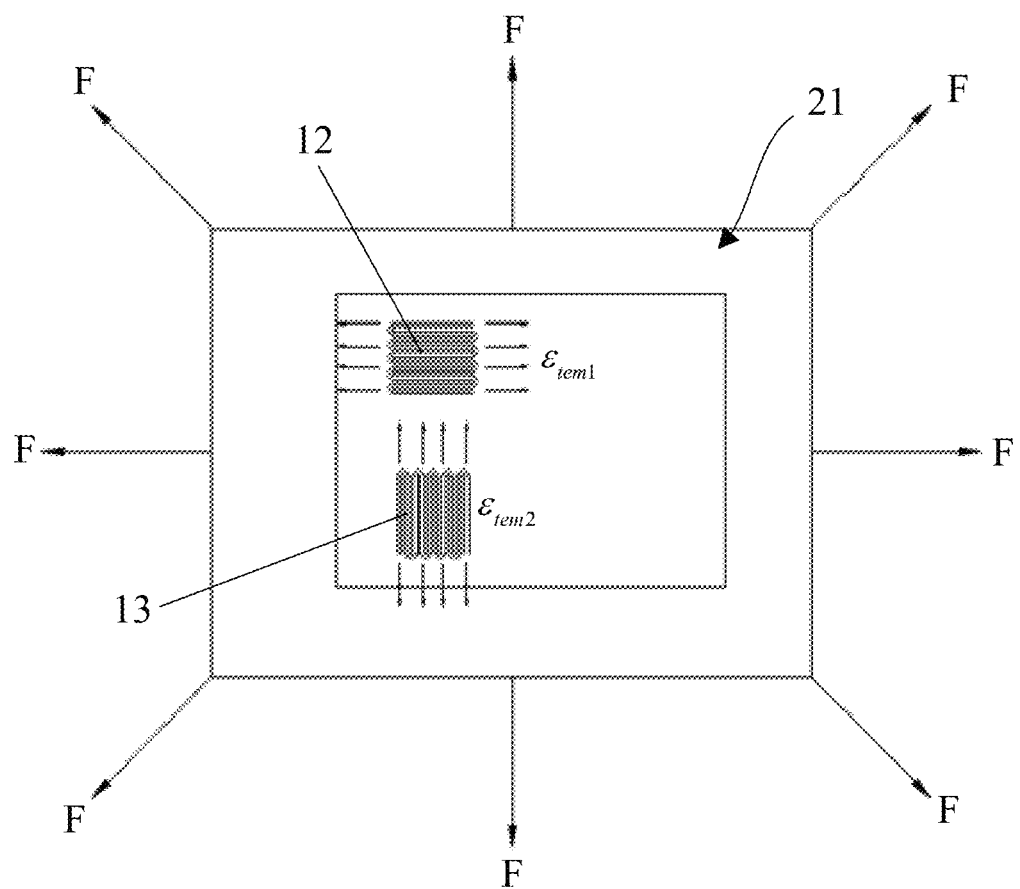
FIG. 9 is a strain schematic diagram of a grid filament when the elastic body according to Embodiment 1 of the present application is subjected to a thermal expansion.

Then, referring to FIG. 9, when the elastic body 21 of the force sensor 20 is thermally expanded, the elastic body 21 is subjected to the tension F in each direction, but the amount of expansion in each direction is the same. The grid filaments of the longitudinal sensitive grid 12 and the lateral sensitive grid 13 are both stretched, and the resistances of R1 and R2 are increased, thereby respectively generating positive strains $\varepsilon_{tem1}$ and $\varepsilon_{tem2}$. $\varepsilon_{tem1}$ corresponds to the longitudinal sensitive grid 12, and $\varepsilon_{tem2}$ corresponds to the lateral sensitive grid 13. Moreover, the $\varepsilon_{tem1}$ and $\varepsilon_{tem2}$ are equal in value. From the Wheatstone half-bridge circuit shown in FIG. 4, it can be obtained that the total strain is $\varepsilon_{tem}=\varepsilon_{tem1}-\varepsilon_{tem2}$, i.e., zero. That is, the Wheatstone half-bridge circuit composed of the strain gauges having the longitudinal and lateral sensitive grids can completely eliminate the influence of temperature drift.

In addition, when the elastic body 21 is simultaneously subjected to the tensile stress and thermal expansion, the total strain is $\varepsilon_{comb}=\varepsilon_{force}+\varepsilon_{tem}$, where $\varepsilon_{tem}$ is always zero, therefore, $\varepsilon_{comb}=\varepsilon_{force}$.

In addition, this embodiment only gives the strain results of the elastic body that is subjected to tensile stress and thermal expansion. However, the foregoing derivation processes are also applicable to the case in which the elastic body is pressed and cooled.

Embodiment 2

The strain gauge and the force sensor provided in this embodiment are almost the same as those in Embodiment 1, and the following description is only for different points.

In order to reduce the number of strain gauges used on the elastic body, the inventor finds that at least two longitudinal sensitive grids can be disposed on one substrate, which can also ensure the actual requirements of contact force measurement. For ease of description, the technical solutions of this embodiment are further described by taking two longitudinal sensitive grids as an example.

Figure 10:
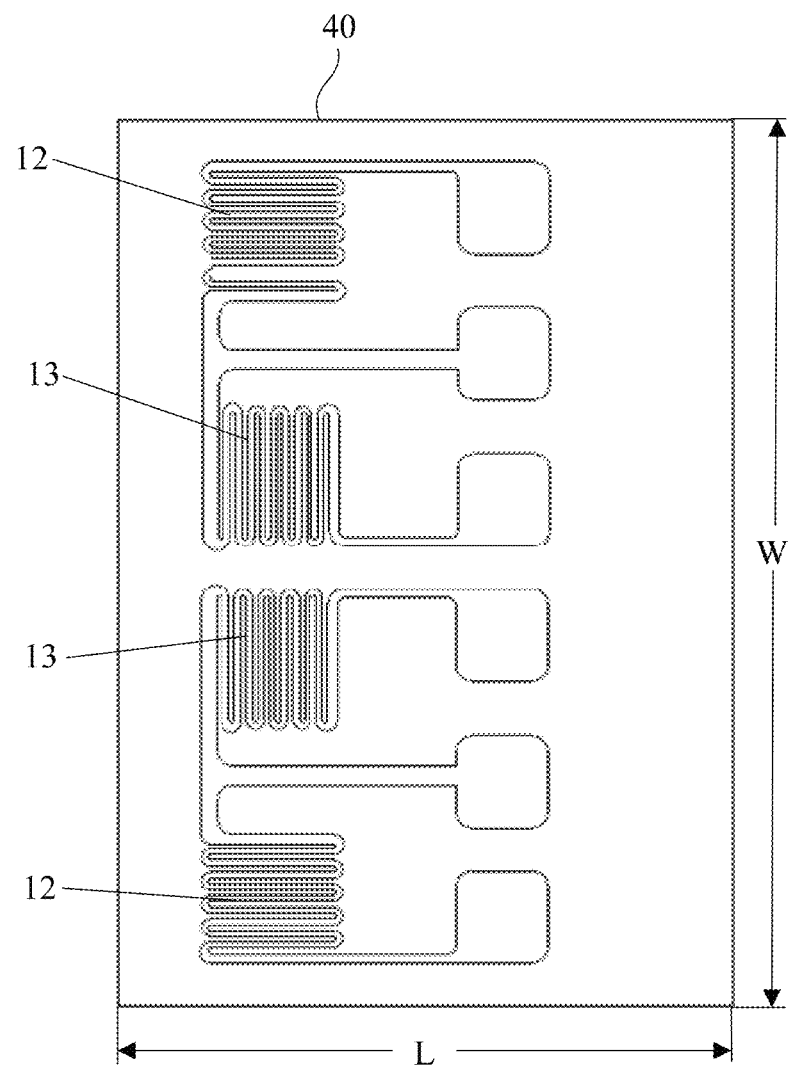
FIG. 10 is a schematic structural diagram of a strain gauge including two longitudinal sensitive grids and two lateral sensitive grids according to Embodiment 2 of the present application.

In one approach, as shown in FIG. 10, two longitudinal sensitive grids 12 are parallel to and in aligned with each other long the width direction of the substrate, and are arranged spaced apart. Moreover, the installation direction of the two longitudinal sensitive grids 12 is parallel to the length direction of the substrate (i.e., the direction of the grid length L' of the longitudinally sensitive grid 12 is parallel to the length direction of the substrate). Two lateral sensitive grids 13 spaced apart in the width direction of the substrate are disposed between the two longitudinal sensitive grids 12. The two lateral sensitive grids 13 are parallel to and aligned with each other, and the mounting direction of the lateral sensitive grids 13 is parallel to the width direction of the substrate (i.e., the direction of the grid length L' of the lateral sensitive grid 13 is parallel to the width direction of the substrate).

In FIG. 10, one of the lateral sensitive grids 13 forms a group with one longitudinal sensitive grid 12 adjacent thereto, and the other one of the lateral sensitive grids 13 also forms a group with the other longitudinal sensitive grid 12 adjacent thereto. Moreover, in each group, the two sensitive grids share one grounding interface. Therefore, the strain gauge 40 formed by the four sensitive grids actually has six interfaces, so that there are many wires connected to the interfaces, and the width size of the strain gauge 40 is relatively large. The width W of the strain gauge 40 is increased by about one time the width W of the strain gauge 10 in Embodiment 1.

Figure 11:
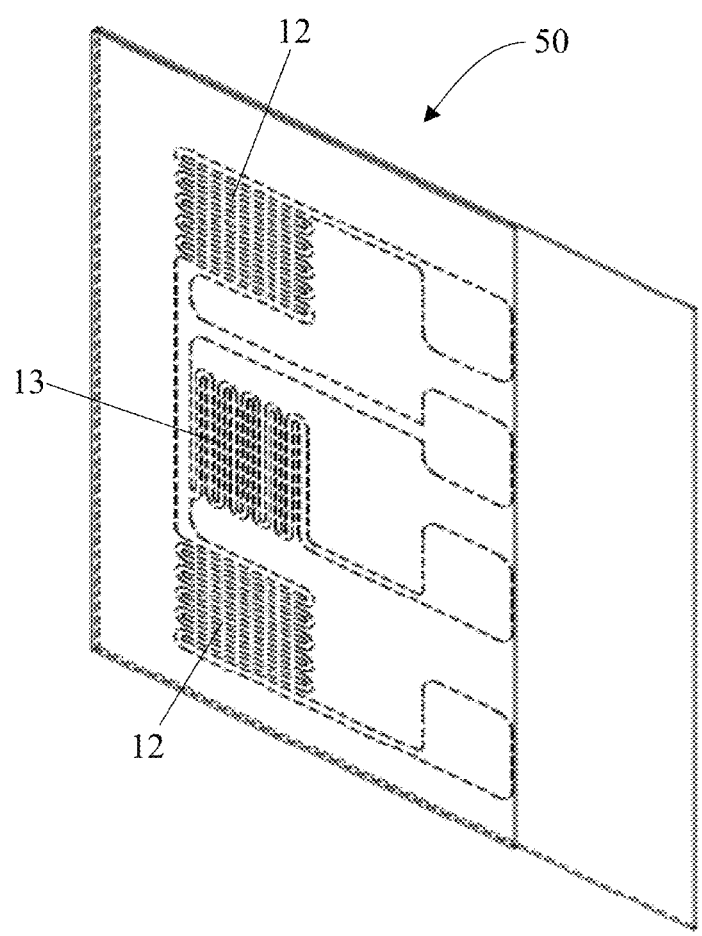
FIG. 11 is a schematic structural diagram of a preferred strain gauge according to Embodiment 2 of the present application.
Figure 12:
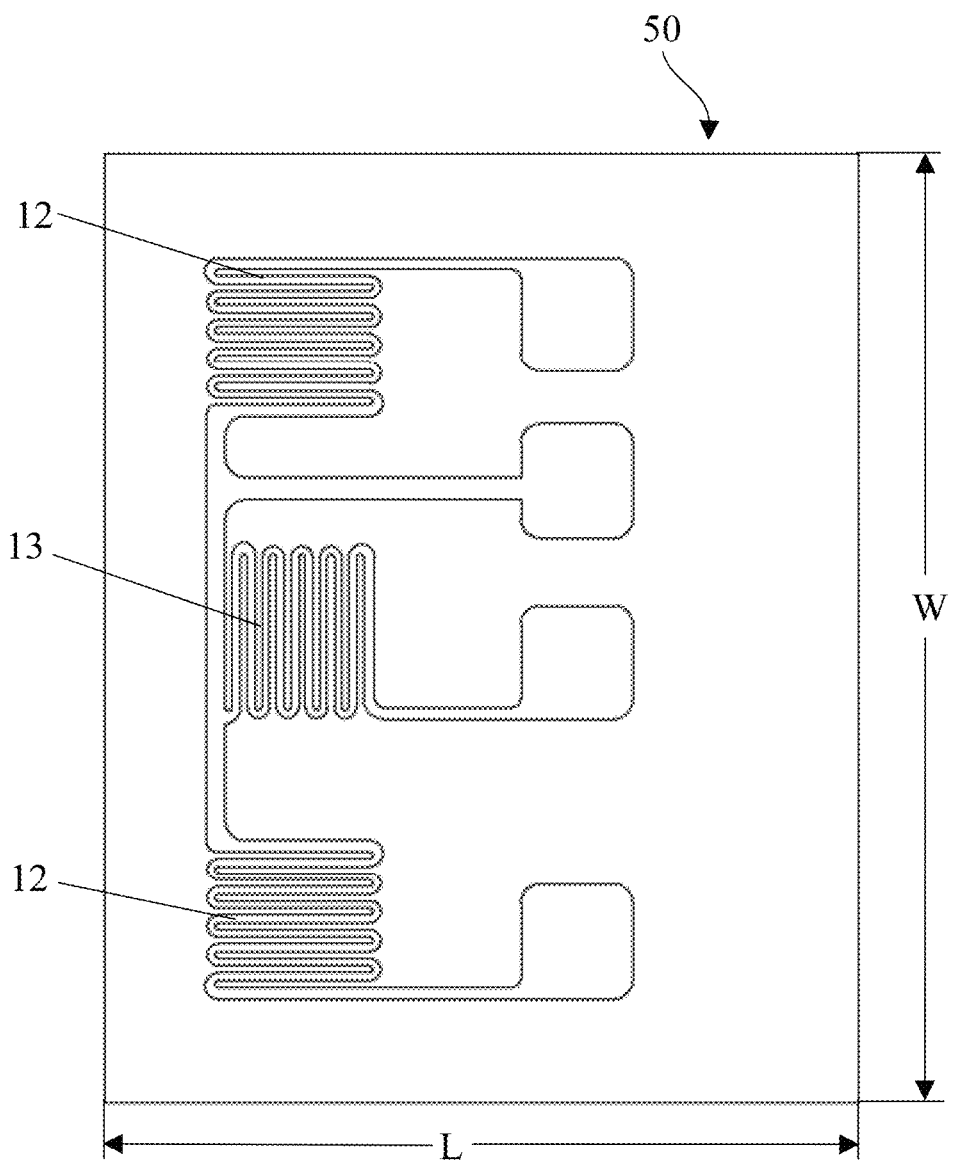
FIG. 12 is a top view of the strain gauge shown in FIG. 11.

In another approach, as shown in FIG. 11 and FIG. 12, the two longitudinal sensitive grids 12 are spaced apart in the width direction of the substrate, and are parallel to and aligned with each other. Only one lateral sensitive grid 13 is arranged between the two longitudinal sensitive grids 12, so that the two longitudinal sensitive grids 12 share one lateral sensitive grid 13, and the two longitudinal sensitive grids 12 share one grounding interface with the lateral sensitive grid 13. Therefore, the strain gauge 50 composed of the three sensitive grids actually requires only four ports. That is, there are only four wires needed for connection. Therefore, the number of wires used is relatively small, and the width W of the strain gauge 50 can be limited to 2 mm or less to obtain a small size of strain gauge 50. In this embodiment, the strain gauge 50 can reduce two 38 AWG wires compared to the foregoing strain gauge 40, which further save the wiring space inside the catheter.

Figure 13:
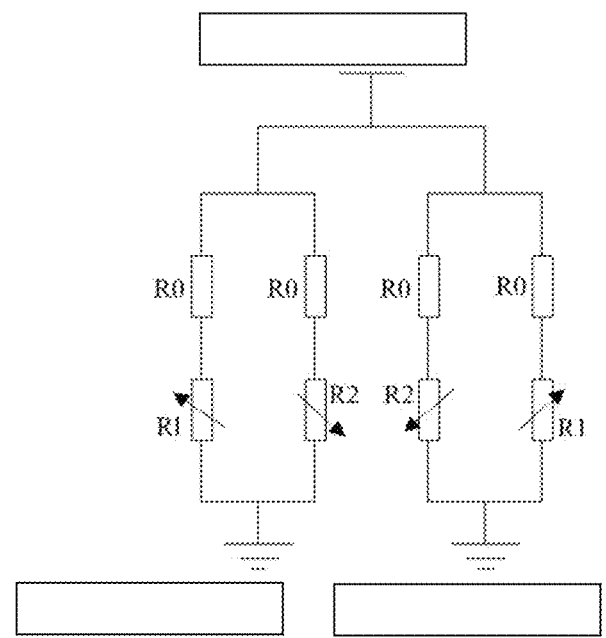
FIG. 13 is a Wheatstone half-bridge circuit composed of the strain gauge shown in FIG. 10.
Figure 14:
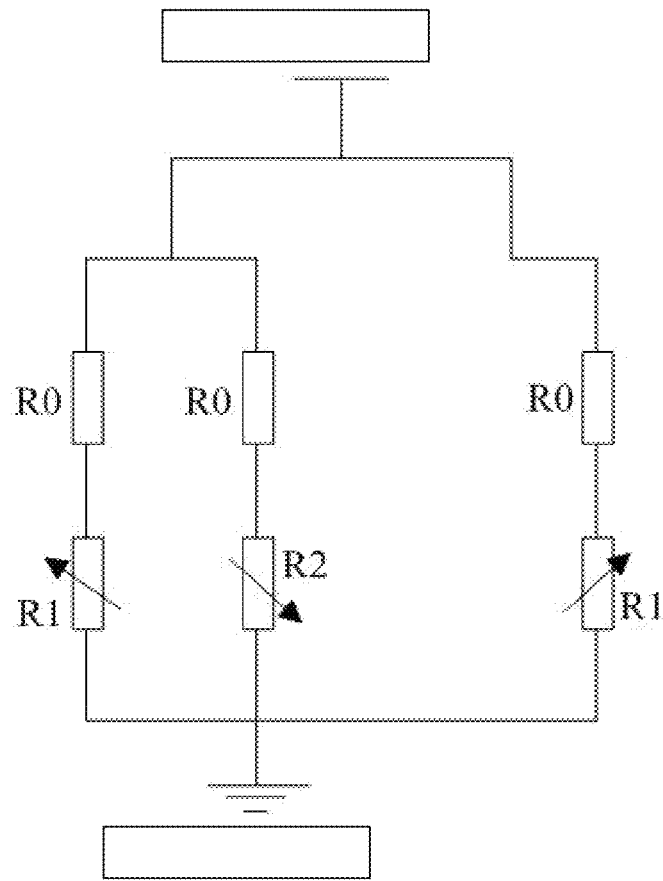
FIG. 14 is a Wheatstone half-bridge circuit composed of the strain gauge shown in FIG. 12.

In addition, FIG. 13 also provides a Wheatstone half-bridge circuit formed by the strain gauge 40 shown in FIG. 10, and FIG. 14 provides another Wheatstone half-bridge circuit formed by the strain gauge 50 shown in FIG. 11 and FIG. 12. R0 is a fixed resistor, the resistor R1 with an upward arrow refers to the longitudinal sensitive grid 12, and the resistor R2 with a downward arrow refers to the lateral sensitive grid 13. It is obvious that the Wheatstone half-bridge circuit provided in FIG. 14 has a more simple structure and a less wiring, and is more convenient to be calculated.

Figure 15:
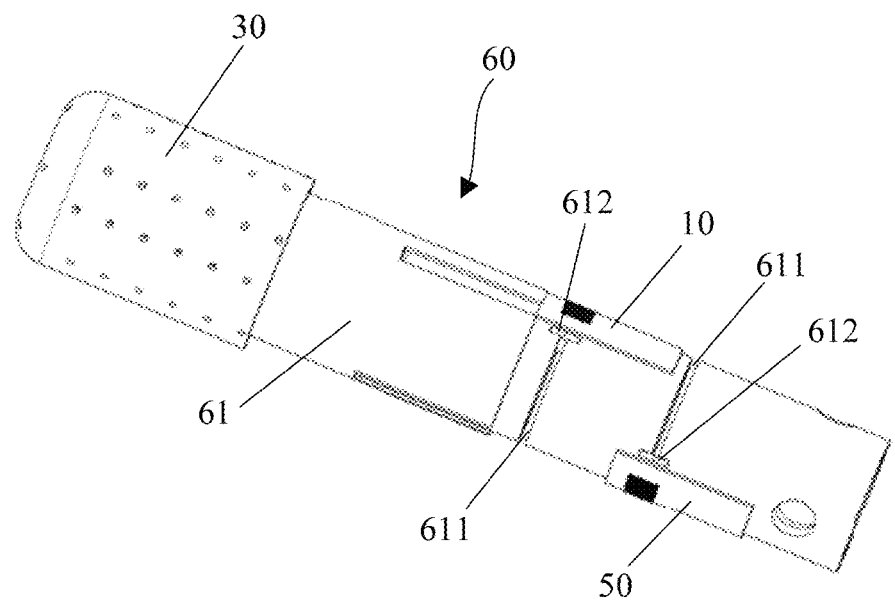
FIG. 15 is a schematic structural diagram of a force sensor according to Embodiment 2 of the present application in connection with an electrode.
Figure 16:
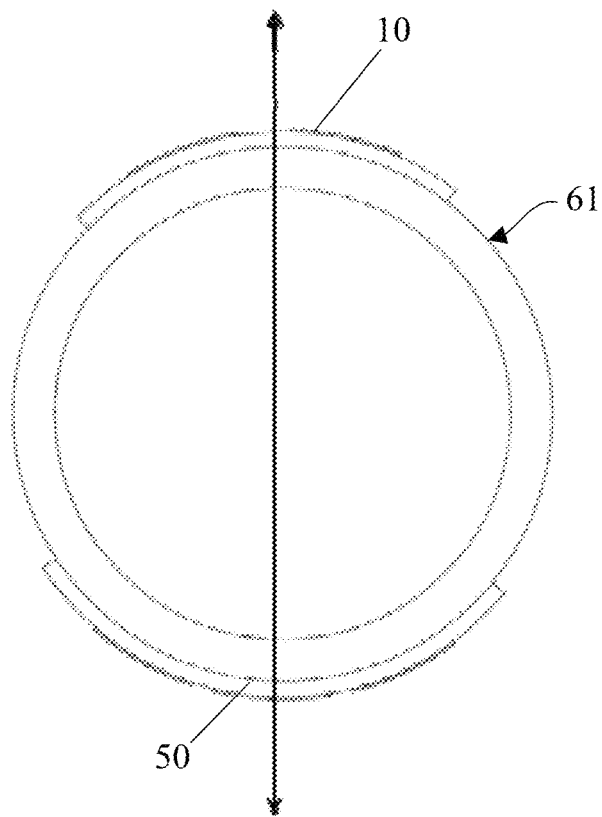
FIG. 16 is a right view of the force sensor of FIG. 15.

Further, this embodiment also provides a force sensor 60, specifically as shown in FIG. 15 and FIG. 16. Only the points different from the force sensor 20 in Embodiment 1 are described below.

The force sensor 60 includes an elastic body 61 and at least two strain gauges disposed on the elastic body 61. The at least two strain gauges are arranged on different circumferences of the elastic body 61 along the axial direction and are circumferentially arranged in a staggered manner. For example, the two strain gauges are a first strain gauge and a second strain gauge. The first strain gauge is the strain gauge 10 of Embodiment 1, and the second strain gauge is the strain gauge 50 of Embodiment 2. That is, the strain gauge 10 includes one substrate, one longitudinal sensitive grid 12, and one lateral sensitive grid 13. The strain gauge 50 includes another substrate, at least two longitudinal sensitive grids 12, and at least one lateral sensitive grid 13.

Different from the foregoing force sensor 20, the two strain gauges, composed of the first strain gauge and the second strain gauge, can also sense the strain at three different positions on the elastic body 61, thereby ensuring the actual requirements of the contact force measurement. However, it is advantageous to reduce the actual number of strain gauges used on the force sensor 20. Therefore, the axial length of the elastic body 61 can be shorter, and accordingly, the length of the interventional medical catheter with the force sensor 60 can also be shortened, thereby saving the cost of use.

Then, the number of hollow grooves 611 formed on the elastic body 61 in the circumferential direction can be reduced to at least two, preferably two, to meet the basic measurement requirements. Therefore, the length of the elastic body 61 is shorter than the conventional one. Same as the Embodiment 1, one strain gauge is disposed between opposite ends of each hollow groove 611. Certainly, same as the Embodiment 1, each of opposite ends of each hollow groove 611 is also provided with one axial groove 612.

For the radiofrequency ablation catheter, the distal end is connected to the force sensor 60, and the hardness of the distal end of radiofrequency ablation catheter is higher than that of other parts of the radiofrequency ablation catheter, so that the ablation electrode 30 is able to contact the vessel wall or tissue through the axial pressure. In order to obtain a better flexibility, the length of the distal end of the radiofrequency ablation catheter can be shortened accordingly, which facilitates the bending of the catheter during implantation for smooth introduction.

In a preferred solution, the strain gauge 10 is closer to the end of the force sensor connected to an electrode than the strain gauge 50. In this case, it is advantageous to access the at least four wires connected to the strain gauge 50 to wire holes on the outer surface of the elastic body 61, so as to shorten the wiring route. As shown in FIG. 16, the two strain gauges 10, 50 are preferably uniformly distributed at 180° in the circumferential direction of the elastic body 61.

Finally, based on the foregoing embodiments, the present application also provides an interventional medical catheter, including a catheter and a force sensor connected to the catheter distal end. The force sensor is the force sensor provided in the present application. The interventional medical catheter also includes an electrode coupled to the force sensor. However, the present application does not limit that the electrode connected to the force sensor is an ablation electrode, which can also be a mapping electrode. For brevity, it is assumed in the foregoing description that the force sensor is connected to the ablation electrode. Those skilled in the art should modify the foregoing description, and the description will be applied to other types of electrodes after appropriate modifications in detail. The force exerted by the distal end of the catheter on the vessel wall or tissue causes the vessel wall or tissue to generate a reactive force acting on the catheter distal end. The reactive force is the contact force to be measured by the present application.

In addition, the preferred embodiments of the present application are as described above, but are not limited to the scope disclosed in the foregoing embodiments. For example, it is not limited that one substrate is provided with only two longitudinal sensitive grids. Three or more longitudinal sensitive grids can also be provided, as long as two adjacent longitudinal sensitive grids share one lateral sensitive grid. Preferably, the plurality of longitudinal sensitive grids are parallel to and aligned with one another, and the lateral sensitive grid and the longitudinal sensitive grid are parallel to and aligned with one another. In addition, the plurality of hollow grooves that are arranged on different circumferences and are not staggered in the circumferential direction can form a set of hollow grooves, and one strain gauge can be disposed between opposite ends of the set of hollow grooves.

In summary, in the strain gauge, the force sensor and the interventional medical catheter provided in the present application, all sensitive grids of the strain gauge share one grounding interface allowing to reduce the number of grounding interfaces on the strain gauge. Therefore, the present application can not only save the wiring space for mounting the strain gauge on the interventional medical catheter, to facilitate the successful mounting of the strain gauge on the interventional medical catheter and to improve the adaptability of the strain gauge, but also reduce the size of the strain gauge, which in turn shortens the length of the elastic body of the force sensor as well as reduces the size of the interventional medical catheter.

Moreover, according to a preferred embodiment of the present application, a plurality of longitudinal sensitive grids are able to be arranged on one substrate of one strain gauge, the plurality of longitudinal sensitive grids being arranged along a same direction one lateral sensitive grid being further arranged between two adjacent longitudinal sensitive grids, all the sensitive grids sharing one grounding interface. Such an arrangement allows to reduce the number of strain gauges used on the force sensor, (i.e., the number of strain gauges is able to be reduced from at least three to at least two), thereby enabling to reduce the length of the force sensor, and in turn shorten the length of the distal end of the interventional medical catheter and cut down the cost of use.

In addition, in the strain gauge according to a preferred embodiment of the present application, all the sensitive grids are configured to share one grounding interface, and the whole size of the strain gauge integrated with the plurality of longitudinal sensitive grids is reduced, so that the length of the hollow groove provided on the elastic body of the force sensor allows to be processed longer along the circumferential direction of the elastic body, and thus the strain gauge located between opposite ends of the hollow groove is able to sense a stronger strain signal. In this case, a better measurement is achieved.

The above description is only for the description of preferred embodiments of the present application, and is not intended to limit the scope of the present application. Any changes and modifications made by those skilled in the art according to the above disclosure are all within the protection scope of the appended claims.

What is claimed is:

1. A force sensor, comprising an elastic body and at least one strain gauge comprising a substrate and a plurality of sensitive grids disposed on the substrate, wherein the plurality of sensitive grids comprise a plurality of longitudinal sensitive grids and at least one lateral sensitive grid, which are arranged in two directions that are perpendicular to each other and share one grounding interface, and the at least one lateral sensitive grid is disposed between two adjacent longitudinal sensitive grids, and all of the longitudinal sensitive grids and the at least one lateral sensitive grid share the grounding interface, wherein the at least one strain gauge is disposed on the elastic body, wherein a plurality of hollow grooves are formed on the elastic body, each hollow groove extending along a circumferential direction of the elastic body, wherein the plurality of hollow grooves are located on different circumferences along an axial direction of the elastic body and are circumferentially arranged in a staggered manner, and the at least one strain gauge is disposed between opposite ends of one of the plurality of hollow grooves.

2. The force sensor according to claim 1, wherein a plurality of strain gauges are provided, and the plurality of strain gauges are arranged on different circumferences along the axial direction of the elastic body and are circumferentially arranged in a staggered manner, the longitudinal sensitive grids of the respective plurality of strain gauges are arranged along the axial direction of the elastic body; and the at least one lateral sensitive grid of the respective plurality of strain gauges are arranged along the circumferential direction of the elastic body.

3. The force sensor according to claim 2, wherein orthographic projections of the plurality of strain gauges in a same plane in the axial direction are uniformly distributed in the circumferential direction.

4. The force sensor according to claim 2, wherein the plurality of strain gauges are provided, and the plurality of strain gauges comprise at least a first strain gauge and a second strain gauge, wherein the first strain gauge is the strain gauge comprising one substrate, one longitudinal sensitive grid and the at least one lateral sensitive grid, the one longitudinal sensitive grid being arranged along the axial direction of the elastic body, the one lateral sensitive grid being arranged along the circumferential direction of the elastic body, and the second strain gauge is the strain gauge comprising another one substrate, a plurality of longitudinal sensitive grids, and at least one lateral sensitive grid, the plurality of longitudinal sensitive grids being parallel to and aligned with each other and arranged along the axial direction of the elastic body, the at least one lateral sensitive grid being disposed between two adjacent longitudinal sensitive grids, the at least one lateral sensitive grid being arranged along the circumferential direction of the elastic body, and wherein all of the longitudinal sensitive grids and the lateral sensitive grids of the second strain gauge share one grounding interface.

5. An interventional medical catheter, comprising a catheter distal end and an electrode, wherein the catheter distal end is provided with the force sensor according to claim 4, and the electrode is coupled to the force sensor, wherein the first strain gauge is closer to the electrode than the second strain gauge.

6. The force sensor according to claim 1, wherein each of the opposite ends of each hollow groove is provided with one axial groove that extends along the axial direction of the elastic body.

7. The force sensor according to claim 6, wherein the sensitive grid of the strain gauge is aligned with the axial groove along the axial direction of the elastic body.

8. An interventional medical catheter, comprising a catheter distal end, wherein the catheter distal end is provided with the force sensor according to claim 1.

9. The force sensor according to claim 1, wherein the substrate has a first direction and a second direction, the first direction being one of a length direction of the substrate and a width direction of the substrate, the second direction being another one of the length direction of the substrate and the width direction of the substrate; and wherein the plurality of longitudinal sensitive grids are disposed along the first direction, and the at least one lateral sensitive grid is disposed along the second direction.

10. The force sensor according to claim 9, wherein the plurality of longitudinal sensitive grids are parallel to and aligned with each other and arranged along the first direction, and
wherein a grid width of the longitudinal sensitive grid is aligned with a grid length of the at least one lateral sensitive grid, or a grid length of the longitudinal sensitive grid is aligned with a grid width of the at least one lateral sensitive grid.

11. The force sensor according to claim 10, wherein all of the sensitive grids share one grounding lead, the grounding lead being connected to the grounding interface, and all of the sensitive grids are integrally formed.

12. The force sensor according to claim 11, wherein the one shared grounding lead is located on a medial axis of the substrate, and the medial axis is parallel to the length direction of the substrate or the width direction of the substrate.

13. The force sensor according to claim 11, wherein each sensitive grid further has one non-grounding interface, and the one non-grounding interface of each sensitive grid is connected to one non-grounding lead, and wherein all of the grounding leads and all of the non-grounding leads are arranged in parallel and extending towards a same direction.

14. The force sensor according to claim 13, wherein the longitudinal sensitive grids and the at least one lateral sensitive grids are equal in grid width and grid length, and all of the longitudinal sensitive grids and the at least one lateral sensitive grids have a same grid structure.

15. The force sensor according to claim 1, wherein the substrate is a semi-rigid substrate.

16. The force sensor according to claim 15, wherein a material of the substrate is selected from one or more of the group consisting of polyimide and polyetheretherketone.

17. The force sensor according to claim 1, wherein each of a length of the substrate and a width of the substrate is not greater than 2.0 mm.

* * * * *